United States Patent
Göttlicher et al.

(10) Patent No.: US 6,482,610 B1
(45) Date of Patent: Nov. 19, 2002

(54) METHOD FOR PRODUCING AGENTS FOR TREATING TUMOR DISEASES AND FOR IMMUNOSUPPRESSION

(75) Inventors: Martin Göttlicher, Stutensee (DE); Siva Kumar Kolluri, San Diego, CA (US); Carsten Weiss, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/646,335

(22) PCT Filed: Feb. 25, 1999

(86) PCT No.: PCT/EP99/01205

§ 371 (c)(1), (2), (4) Date: Nov. 6, 2000

(87) PCT Pub. No.: WO99/47703

PCT Pub. Date: Sep. 23, 1999

(30) Foreign Application Priority Data

Mar. 16, 1998 (DE) .......................... 198 11 326

(51) Int. Cl.[7] .................. C12N 15/00; C12Q 1/68; C07H 21/04
(52) U.S. Cl. ................... 435/69.1; 435/6; 536/24.1
(58) Field of Search ............. 424/93.21; 435/6, 435/69.1; 536/24.1

(56) References Cited

U.S. PATENT DOCUMENTS 5,650,283 A   7/1997  Bradfield et al.
5,854,010 A * 12/1998  Denison et al. ................ 435/8

OTHER PUBLICATIONS

McDougal et al. Cancer Lett 1997 Nov; 53–63.*

Safe et al. Toxicology Lett 1998; 102–103:343–47.*

Wang et al. Arch Biochem Biophy 1998 Aug; 356:239–48.*

Kolluri K et al: "TCDD–Induced Cell Cycle Delay Requires AH–Receptor–Dependent . . . . ", BD. 355, No. 4, 1997 XP002106040.

Bradfield C A et al: "Nucleic Acids Encoding Murine and Human AH Receptors" BD. 13, No. 4, Jan. 1, 1995, PP. 728–729 XP004044987.

(List continued on next page.)

Primary Examiner—James Ketter
Assistant Examiner—Q Janice Li
(74) Attorney, Agent, or Firm—Friedrich Kueffner

(57) ABSTRACT

The invention relates to a process for preparing agents which are suitable for treating tumour diseases or for immunosuppression, with target cells being treated with chemical compounds which bind to the Ah receptor of the target cells, the binding of the chemical compound(s) to the Ah receptor of the target cells being determined by measuring the expression, which is induced thereby, of a detector gene which is relevant for the effects of the chemical compound(s), and the chemical compound(s) which has/have been found in this way being used for preparing the agent(s).

6 Claims, 4 Drawing Sheets

OTHER PUBLICATIONS

Göttlicher M et al: "Die Molekulare Basis der Wirkungen des Umweltgiftes . . " BD. 29, No. 3 1997, PP. 211–220, XP002106041.

Zacharewski, T R et al: "Antoesstrogenic Effect of 2, 3, 7, 8 . . . . . " BD. 54, 1994, PP. 2707–2713, XP002106042.

Polyak K et al: "Cloning of P27KIPL, A Cyclin–Dependent Kinase Inhibitor . . " BD. 78, 1994, PP. 59–66, XP002106043.

Taeg K K et al: "Characterization of the Murine Cyclin–Dependent . . . . . " BD. 180, No. 1–2, Nov. 21, 1996, PP. 113–120 XP004071904.

Minami S et al: "Molecular Cloning and Characterization of the Human . . . . " BD. 411, 1997, PP. 1–6, XP002106044.

Fredersdorf S et al: "High Level Expression of p27 (Kipl) and Cyclin . . . . " BD. 94, No. 94, Jun. 1997, PP. 6380–6385, XP002100142.

Weiss C et al: "Retroviral Expression of AH Reeptor Reconstitutes . . . . " BD. 353, No. 4, 1996, P R124 XP002106045.

Kolluri S K: Search for AH Receptor Target Genes Which Mediate Dioxin . . . . BD. 6201, 1999, PP. 1–109, XP002106046.

Denison M S et al: "Carbarly, A Carbamate Insecticide, is a Ligand for . . . . " BD. 152, 1998, PP. 406–414 XP002106047.

Kolluri S K et al: "Cell Cycle Control by Dioxins is Mediated by . . . . . . . " BD. 357, No. 4, 1998, PP. R151, XP002106048.

* cited by examiner

METHOD FOR PRODUCING AGENTS FOR TREATING TUMOR DISEASES AND FOR IMMUNOSUPPRESSION

BACKGROUND OF THE INVENTION

The invention relates to a process for preparing agents for treating tumour diseases and for immunosuppression. The agents selected in this context are those which exhibit particularly effective binding to the Ah receptor.

The Ah receptor is a member of the bHLH-PAS protein family. The members of this protein family act as conditionally regulated transcription factors which are activated by various chemical compounds, for example by dioxins, aromatic hydrocarbons, (heterocyclic) food mutagens and the like. In that which follows, such chemical compounds which activate the Ah receptor are also termed Ah ligands.

Ah ligands transform the Ah receptor into an active state in which the Ah receptor dimerizes, for example, with the nuclear factor ARNT and, as a consequence, induces the expression of target genes. To date, it is known that target genes which correlate with the metabolism of foreign substances are expressed. These include the cytochrome P450I subfamily and enzymes of phase II metabolism (Schmidt, J. V. et al., Ann. Rev. Cell Dev. Biol. 12, 55 (1996); Hankinson, Annu. Rev. Pharmacol. Toxicol. 35, 307 (1995)). It is furthermore known that dioxins exert an influence on the proliferation and differentiation of cells, with phenomenological effects of this influence which may be mentioned by way of example being augmented differentiation of the skin, reduced body growth, thymus atrophy, inhibition of spermatogenesis and carcinogenesis (e.g. of the liver in rodents). The Ah receptor plays a role in these processes, as is demonstrated by the correlation between Ah receptor activation and the toxicity of dioxin-related ligands and also by genetic investigations carried out on mice which carry different alleles of the Ah receptor gene or targeted null mutations (Schmidt, loc. cit.; Hankinson, loc. cit.; Fernandez-Salguero, et al. Science 268, 722 (1995); Sewall, et al. Mutat. Res. 333, 111 (1995). It is unlikely that a dioxin-induced metabolism of foreign substances is responsible for the effects of dioxins on cell proliferation and differentiation. The mechanisms and genes by which the Ah receptor exhibits the abovementioned pronounced effects in this regard are so far unknown. While IL-1 and tissue plasminogen activator inhibitor 2 have been identified as being target genes for the Ah receptor (Sutter, et al. Science 254, 415 (1991)), these genes appear, like those of other cytokines, not to be regulated directly by the Ah receptor.

It is known that the cell cycle inhibitor gene p27-Kip1 is a factor for regulating cell proliferation (Polyak et al. Cell 78, 59 (1994); Loda et al. Nat. med. 3,231 (1997); Porter et al. Nat. med. 3, 222 (1997); Catzavelos et al. Nat. Med. 3, 227 (1997); Fredersdorf et al. Proc. Natl. Acad. Sci. USA 94, 6380 (1997). This follows from investigations which have shown that the expression of Kip1 is reduced in various forms of tumour. Kip1 is consequently a tumour suppresser gene. It would therefore be desirable to find substances which are able to increase the cellular level of the protein which is expressed by the Kip1 gene. To date, it is known to use transforming growth factor β (TGFβ); however, this factor only stabilizes the protein expressed by the Kip1 gene and does not induce Kip1 messenger RNA.

SUMMARY OF THE INVENTION

In relation to the prior art, the invention is based on the technical problem of making available a process for preparing agents which are suitable for treating tumour diseases or for immunosuppression.

For solving this technical problem, the invention teaches that target cells are treated with chemical compounds which bind to the Ah receptor of the target cells, that the binding of the chemical compound(s) to the Ah receptor of the target cells is determined by measuring the expression, which is induced thereby, of a detector gene which is relevant for the effects of the chemical compound(s), and that the chemical compounds which have been found in this way are employed for preparing the agent.

The detector gene is preferably under the control of the regulatory elements of the Kip1 gene. For example, a gene which is the Kip1 gene product which is naturally controlled by the Kip1 promoter is described as being a detector gene. In this case, Kip1 expression can be detected, for example, using Northern blot or Western immunoblot methods. In this context, the expression detector gene refers to the fact that a protein which can be expressed thereby can be readily detected at least semiquantitatively using means which are technically customary.

Alternatively, synthetic genes which contain the essential regulatory elements of the Kip1 gene are also suitable. In this case, it is advantageous, for example, to use the luciferase gene under the control of the Kip1 promoter since this gene is particularly easy to measure. Luciferase is an enzyme which is present in luminous organs and which converts luciferin into an optically excited state in the presence of oxygen. Luciferase can therefore easily be measured using optical detection systems, which systems can be employed to achieve high sample throughputs and to screen low molecular weight substances efficiently within the context of the process according to the invention. However, it is also possible to conceive of using other detector systems, such as alkaline phosphatase, chloramphenicol acetyltransferase or β-alactosidase, for the process according to the invention.

The invention is accordingly based on the novel finding that the Ah receptor directly induces expression of the Kip1 gene, more specifically its transcription, and that use can be made of a detector gene which is under the control of the Kip1 gene.

Using the process according to the invention, it is possible, on the one hand, to determine agents for treating tumour diseases. On the other hand, it is possible to investigate which chemical compounds, by means of inducing expression of the Kip1 gene, are suitable for use as tumour suppresser substances (and are not merely protein-stabilizing as is TGFβ). The chemical compounds which are found in this way are advantageous as compared with TGFβ since they are comparitively simpler to produce (namely by means of organic synthesis instead of using recombinant methods) and employ as pharmaceutical active compounds. Their simpler employment is based on the fact that such chemical compounds have the potential to be effective following oral administration. It is furthermore advantageous that the chemical compounds that can be found in this way are inducers of Kip1 messenger RNA and not merely of protein stability. Thus, adequate expression of the messenger RNA is a primary requirement for enabling accumulation of the Kip1 protein in cells to be further increased by means of protein stabilization.

According to the above, therefore, the process according to the invention is suitable for screening both chemical compounds for treating tumour diseases and chemical compounds for immunosuppression. The tested agents which are selected in this context are those which exhibit a particularly effective induction of the Kip1 gene.

The chemical compounds which are found using the process according to the invention are also better tolerated than is TGFβ since the latter also promotes inflammatory reactions, for example. While side-effects, such as immunosuppression and the induction of foreign substance-degrading enzymes, are also to be expected when using the found substances, these side-effects are comparatively acceptable. Moreover, substances which are found using the process according to the invention can also be employed for treating immune diseases such as lymphoproliferative syndromes or autoimmune diseases, or in association with transplantations, since the cellular (T-cell) immune system, in particular, can be suppressed by Ah ligands.

The present invention consequently also relates to chemical compounds which are suitable for preparing agents for treating tumour diseases or for immunosuppression. These agents are characterized in that they can be selected by treating target cells with chemical compounds which bind to the Ah receptor of the target cells and determining the binding of the chemical compounds to the Ah receptor of the target cells by measuring the expression, which is induced thereby, of a detector gene which is relevant for the effects of the chemical compounds. That which has been said above applies with regard to the detector genes and promoters which can be used in this context.

The invention furthermore relates to transgenic target cells for use in the process according to the invention. All the comments which have been made above with regard to promoters and detector gene DNA apply in this context in a corresponding manner. These target cells can readily be prepared using recombinant DNA methods. For example, the cDNA sequence of the detector gene DNA can be cloned into an expression vector, for example a plasmid, which contains the promoter region of the Kip1 gene.

The DNA sequence of luciferase, for example, is known (de Wet, J. R. et al., Mol. Cell. Biol. 2, 725–737). The DNA sequence of the Kip1 promoter is likewise known, see Kwon, T. K. et al. Gene 180, 113 (1996); Minami, S. et al. FEBS Letters 411, 1 (1997). Customary methods are used to arrange the Kip1 promoter and the detector gene in relation to each other.

Selection genes can additionally be introduced into the target cell for the purpose of monitoring the gene transfer. These selection genes are genes which allow the transgenic target cells which have been generated to be easily selected.

It is within the customary ability of the skilled person to select suitable target cells. Suitable target cells are microorganisms and animal and human cells. Yeast cells are examples of microorganisms. Examples of suitable animal cells are CHO cells, hepatoma cells or human tumour cell lines.

If the transgenic target cells are not human cells, it can be advantageous if their genome then contains DNA which encodes the expression of the human Ah receptor. This DNA is known, see the literature reference Dolwick, K. M. et al. Mol. Pharmacol. 44, 911–917. For this, the target cells are additionally recombinantly modified so that they express a cDNA which encodes the human Ah receptor. The target cells employed are, for example, cells taken from animals of the rodent group, for example 5 L rat hepatoma cells.

The invention finally also relates to agents which are suitable for treating tumour diseases and for immunosuppression. These agents are characterized that they contain the above-described chemical compounds. They are preferably prepared using target cells in the manner depicted above.

After it had been found by introductory experiments that the effect of dioxin on the cell cycle required gene expression which was continuous and induced, experiments were carried out to investigate the Ah receptor-dependent, cell cycle-regulating genes by characterizing biochemical changes in the course of the cell cycle (Lees, E., Curr. Opin. Cell Biol. 7, 773 (1995); Morgan, D. O., Nature 374, 131 (1995). The levels of cyclins D and E, which are involved in the G1-S transition in the cell cycle, as well as their associated cyclin-dependent kinases (cdks 2 and 4), were not reduced by dioxin treatment (see FIG. 2A). The levels of cyclins D2 and D3 were even raised, presumably because the cells are frozen in a state which is per se associated with a high level of these cyclins. However, cyclin E-associated histone H1 kinase activity was substantially reduced following treatment with TCDD (see FIG. 2B). Following exposure to dioxin for from 4 to 72 hours, the level of p27Kip1 (Polyak. K. et al., Cell 78, 59 (1994); Toyoshima H., Hunter, T., Cell 78, 67 (1994)), which is induced by TGFβ under other conditions, was found by Western blot to be raised in every case (see FIG. 2C, lanes 1 and 2). This induction is specific because the p18-Ink and p21-Cip1 levels were not noticeably altered and it was not possible to detect other inhibitors (p57-Kip2, p15-Ink, p16-Ink and p19-Ink). Following treatment with TCDD, increased quantities of p27Kip1 were associated with cyclin E, as is evident from an immunocoprecipitation analysis (FIG. 2D). The expected accumulation of a slowly migrating form of cdk2, which is presumably not phosphorylated at Thr-160 (Polyak, loc. cit.), was found in the same precipitates (FIG. 2D). AhR (R=receptor) has an influence on induction of p27Kip1 since it was not possible to observe dioxin-dependent upregulation of p27Kip1 in an AhR-poor subclone of 5 L cells (BP8-AhR−, FIG. C, lanes 3 and 4). Furthermore, induction was restored by ectopic expression (Weiss, C. et al., Exp. Cell Res. 226, 154 (1996)) of the AhR in this subclone (BP8-AhR+, FIG. C, lanes 5 and 6). The rise in the level of the p27Kip1 protein was accompanied by a fourfold induction of Kip1 mRNA (FIG. 2E, lanes 1 and 2). This is not caused by RNA stabilization since TCDD did not affect the breakdown of Kip1 mRNA following interruption of its transcription by actinomycin D. Induction of Kip1 mRNA does not require the dioxin-induced expression of intermediate proteins since the translation inhibitor cycloheximide had no effect (FIG. 2E, lanes 3 and 4). These data prove that the AhR-dependent activation of Kip1 transcription is a novel mechanism of Kip1 induction which is different from the accumulation of Kip1 protein due to post transcriptional regulation, as in other cases (Loda, M. et al., Nat. med. 3, 231 (1997), Pagano, M. et al., Science 269, 682 (1995); Tam, S. W., et al., Leukemia 3, 363 (1997)).

Genetic indications of a causal role for Kip1 induction in dioxin-induced cell cycle retardation were obtained by transiently expressing a Kip1 antisense RNA in order to inactivate Kip1. Coexpression of green fluorescent protein (GFP, Heim, A. B. et al., Nature 373, 663 (1997)) enabled flow cytometry to be used to detect efficiently transfected cells (FIG. 3A). When GFP was expressed together with an empty expression vector, TCDD treatment reduced the relative number of cells in S/G2 in both groups, i.e. the efficiently transfected subpopulation (FIG. 3B, upper panel) and the majority of non-transfected cells from the same culture dish (FIG. 3B, second row). When Kip1 antisense RNA was expressed together with GFP, the TCDD effect on cell cycle distribution was interrupted in the efficiently transfected subpopulation of cells (FIG. 3B, third row). In the non-transfected subpopulation from the same cell culture, TCDD retarded the progress of the cell cycle in the expected manner (FIG. 3B, last row). In this context, it is to be noted that the electroporation reduced sensitivity to dioxin such that the observed effects on the cell cycle were less pronounced than in non-transfected cells, for example 1.5–2-fold as compared with 3–4-fold in non-electroporated cells (Weiss, loc. cit.). These data demonstrate clearly that Kip1 is required for the AhR-dependent dysregulation of proliferation of 5 L cells. Interestingly, the loss of Kip1 as a result of site-directed mutagenesis in mice leads to the opposite phenotype following poisoning with dioxin, namely an increase in body weight and multiple organ hyperplasia including a hyperplastic thymus (Fero, M. L. et al., Cell 85, 733 (1996); Nakayama, K., ibid. p. 707; Kiyokawa, ibid. p. 721).

An important target for dioxin toxicity is the thymus, which suffers an AhR-dependent atrophy (Poland, A. et al., Annu. Rev. Pharmacol. Toxicol. 22, 517 (1982); Fernandez-Salguero, P. et al., Science 268, 722 (1995)). Foetal thymus organ culture (FTOC) provides a useful model for studying dioxin activities (Lai, Z. W. et al., Mol. Pharmacol. 52, 30 (1997), and the literature references which are cited therein). After only 2 days of FTOC, a 3-fold induction of Kip1 protein was found in thymocytes which had been prepared from TCDD-treated cultures as compared with cultures which had only been exposed to the solvent (FIG. 4A). This was accompanied by a decrease in the proliferation of the thymocytes, as shown by a reduced incorporation of $^3$H-thymidine into the thymocyte DNA (75±7%) and a drop, from 32±3% down to 24±1%, in the number of cells in the S and G2 phases of the cell cycle (a representative example from 3 similar experiments is shown in FIG. 4B). While the proliferation rate in all the early thymocyte subpopulations was reduced independently of the status of CD4 or CD8 expression (Table 1), the effect was more strongly pronounced in the predominantly immature, double negative subpopulation and in a small CD4low/+/CD8- subpopulation.

In summary, the findings which have been presented show that the cell cycle inhibitor p27Kip1 is under the control of AhR. This surprisingly makes it possible, according to the invention, to compare data on dioxin toxicity in rodents and humans (Sewall, C. H., Lucier G. W., Mutat. Res. 333, 111 (1995)) or toxicity at low dioxin concentrations, as are to be found ubiquitously in the environment.

DESCRIPTION OF PREFERRED EMBODIMENTS

The invention, and the findings on which the invention is based, are explained in more detail below.

Figure 1:
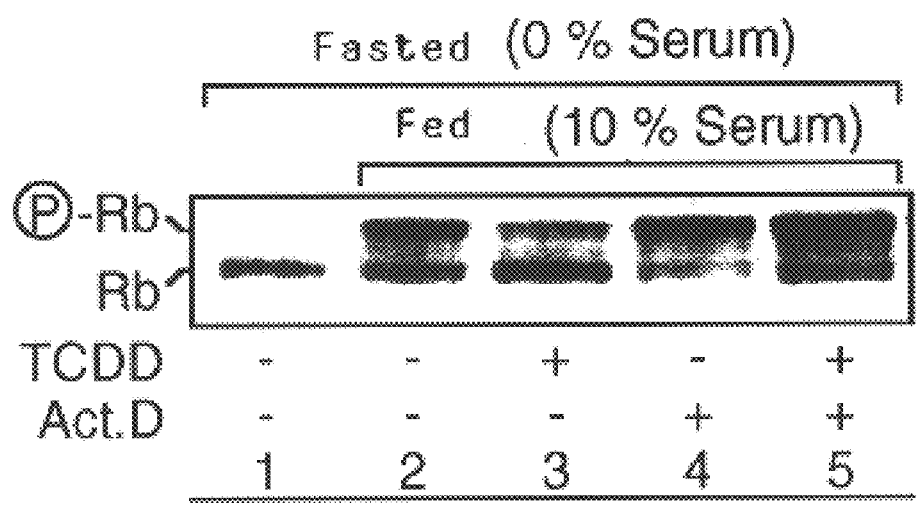
FIG. 1 shows the transcription-dependent retardation in the progress of the cell cycle which is brought about by TCDD.

FIG. 1 shows the transcription-dependent retardation in the progress of the cell cycle which is brought about by TCDD. 5 L cells were frozen in their growth by being fasted in serum-free medium for 24 h and synchronously released from the block in the cell cycle by the addition of serum. The progress in the cell cycle was monitored by Western blot analysis, by determining the accumulation of phosphorylated Rb protein (upper arrow) in relation to hypophosphorylated Rb protein (lower arrow) 8 h after stimulating with the serum. 2 h before the analysis, the cells were treated with 1 nM TCDD, the transcription inhibitor actinomycin D (5 μg/ml) or both these compounds. The culture conditions have been described previously (Weiss, C. et al. Exp. Cell Res. 226, 154 (1996)), and extracts were prepared by lysing the cells in denaturing SDS sample buffer.

Figure 2:
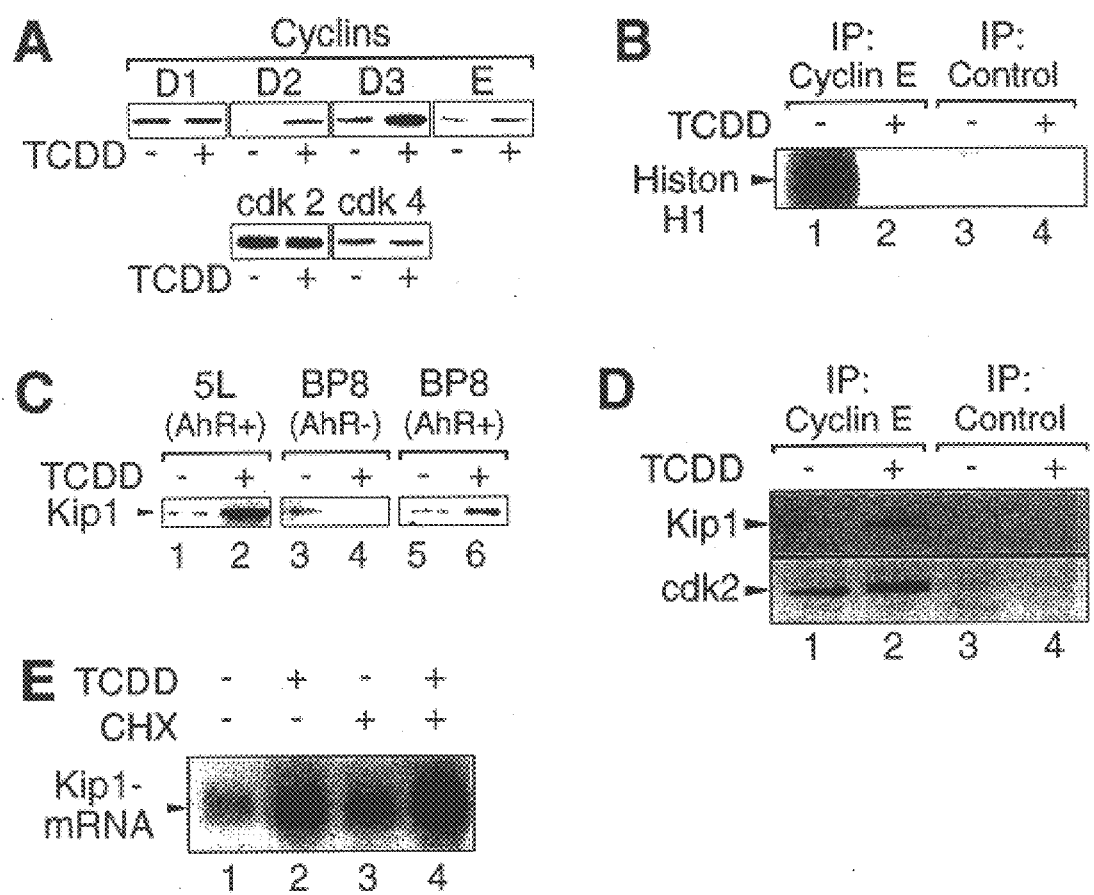
FIG. 2 shows induction of the p27-Kip1 cell cycle inhibitor during the retardation in the TCDD dependent progression of the cell cycle.

FIG. 2 shows induction of the p27Kip1 cell cycle inhibitor during the retardation in the TCDD-dependent progression of the cell cycle. Biochemical properties of G1-phase cyclin/cdk complexes were analysed using 30–60%-confluent, asynchronous cell cultures which, apart from those in section E, had been subjected to a 24-hour treatment with TCDD or 0.1% of the DMSO solvent. The quantities of G1-phase cyclins D1, D2, D3 and E, and also cdks 2 and 4(A) were determined by Western blot in extracts which had been prepared by lysis using a mild detergent (Matsushime, H. et al. Mol. Cell Biol. 14, 2066 (1994)). Cyclin E-dependent histone H1 kinase activity (B) was measured in an immune complex kinase assay (Matsushime, loc. cit.) following precipitation with an anti-cyclin E antibody (lanes 1 and 2) or a corresponding anti-AP-2 antibody as the negative control (lanes 3 and 4). The levels of p27Kip1 protein (C) were determined by Western blot in whole-cell extracts prepared from TCDD-treated cultures of AhR-expressing 5 L wild-type cells, their AhR-deficient BP8AhR-derivatives and BP8 cells which were expressing AhR ectopically (BP8AhR+) (Weiss, loc. cit.). (D) the association of elevated p27Kip1 levels with cyclin E was tested by immunocoprecipitation analysis using an anti-cyclin E antibody, followed by a Western blot analysis of p27Kip1 or cdk2 (Matsushime, loc. cit.). The induction of Kip1 mRNA (E) following a 4-hour exposure to TCDD, with or without a 30-minute pretreatment with the translation inhibitor cycloheximide (20 μg/ml), was tested by Northern blot in 10 μg of total RNA. The partial rat Kip1 cDNA probe was generated by RT-PCR from 5 L-cell RNA using primers which corresponded to nt 28–54 and nt 548–577 of the murine cDNA (Polyak, loc. cit.). The fact that the lanes in protein gels containing whole-cell extracts were uniformly loaded was checked by Coomassie-staining a part of the gel, and the RNA loading was checked by rehybridizing the blot with a GAPDH probe.

Figure 3:
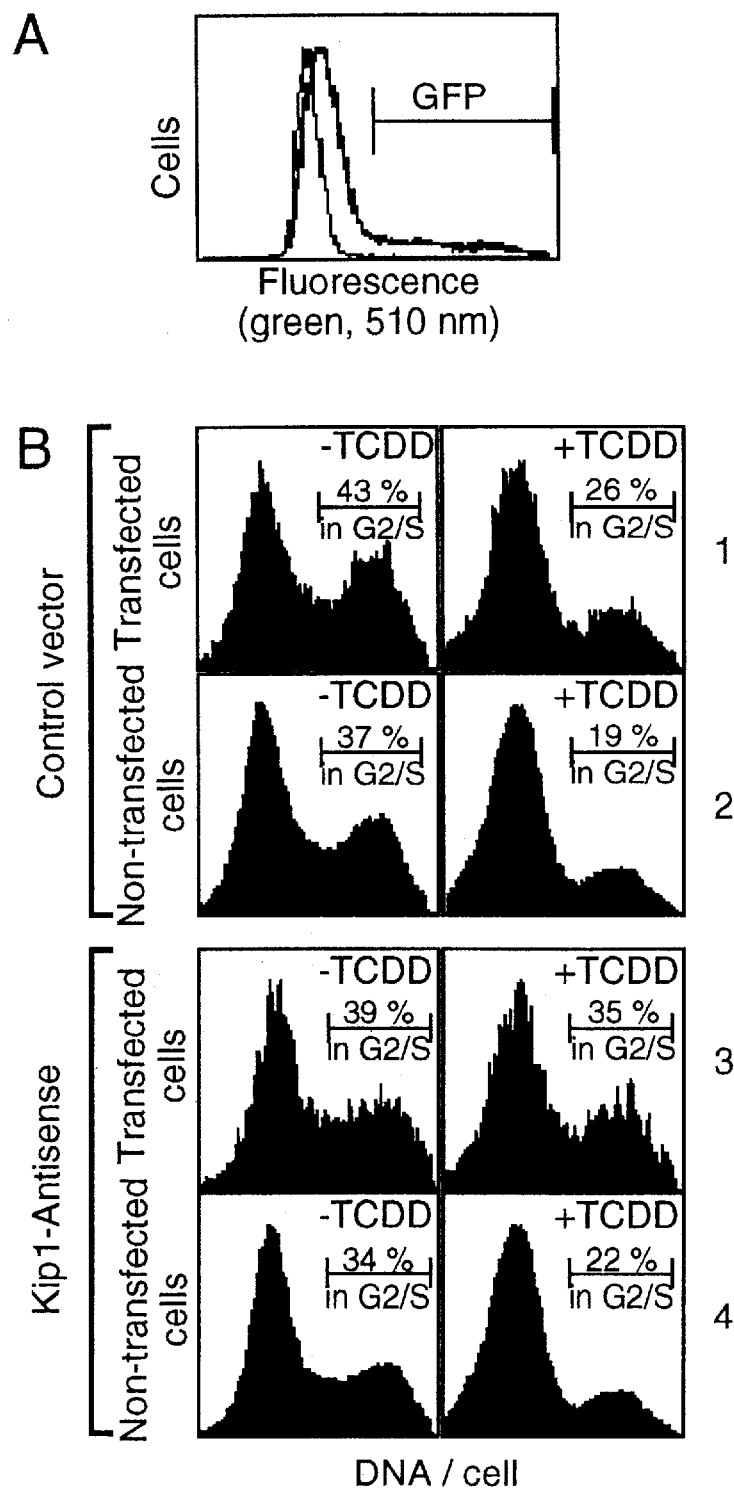
FIG. 3 shows how the expression of the Kip1 antisense RNA affects the TCDD induced retardation on the progress of the cell cycle.

FIG. 3 shows how the expression of Kip1 antisense RNA affects the TCDD-induced retardation in the progress of the cell cycle. 5 L cells were transiently cotransfected with expression vectors for a Kip1 antisence RNA and GFP (part B, lower panel) or with the empty expression vector and GFP (part B, upper panel). 32 h after the transfection, the cells were treated with 1 nM TCDD or 0.1% DMSO solvent, as the control, and harvested, for the analysis by flow cytometry 18 h later, using trypsin. (A) The GFP-expressing subpopulation of transfected cells (thick line) was identified by means of a high green fluorescence (GFP) as compared with untransfected cells (thin line). (B) Cell cycle profiles were determined by staining with H33258 and analysed individually for efficiently transfected (approx. 5%), green-fluorescing subpopulations (rows 1 and 3) and untransfected subpopulations (rows 2 and 4) in the presence of 1 nM TCDD (right-hand panels) or 0.1% DMSO solvent (left-hand panels).

Figure 4:
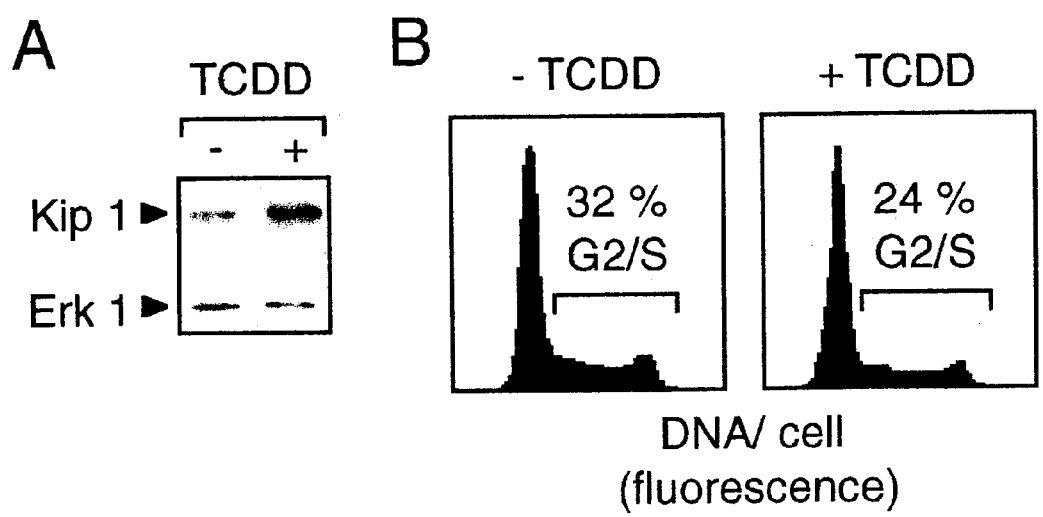
FIG. 4 shows TCDD induced p27-Kip1 protein and cell cycle retardation in foetal thymus organ culture.

FIG. 4 shows TCDD-induced p27Kip1 protein and cell cycle retardation in foetal thymus organ culture. Foetal thymus glands from C57B16 mice were explanted after 14.5 days of pregnancy and cultured for 2 days in the presence of 1 nM TCDD or 0.1% DMSO solvent prior to preparing thymocytes. p27Kip1 protein (A) was determined by Western blot in $10^5$ thymocytes. Uniform loading of the gel was ensured by probing the blots once again with an Erk1 antibody (one of three representative examples is shown). The cell cycle distribution of the total lymphocyte population (B) was determined by means of flow cytometry following DNA staining with H33258 bisbenzimide dye.

The following table shows the suppression of proliferation in thymocyte subpopulations brought about by TCDD. Thymocytes from foetal thymus glands were collected after 2 days of culture in the presence or absence of TCDD and analysed for their cell cycle distribution. The values are mean values±S.D. from 3 independent experiments.

|         | % in G2/S |         |
|---------|-----------|---------|
| Subtype | −TCDD     | +TCDD   |
| CD4−/CD8− | 28 ± 4  | 18 ± 2  |
| CD4+/CD8− | 39 ± 5  | 24 ± 4  |
| CD4−/CD8+ | 45 ± 9  | 32 ± 6  |
| CD4+/CD8+ | 42 ± 12 | 35 ± 10 |

What is claimed is:

1. A process for selecting a compound which is a candidate for a therapeutic agent suitable for treating tumor diseases or immunosuppression, comprising selcecting a chemical compound which binds to a Ah receptor and induces Kip1 promoter controlled gene expression, by i) treating target cells with the chemical compound which binds to the Ah receptor on the surface of the target cells, and ii) determining the binding of the chemical compound to the Ah receptor by measuring the expression of detector genes which are under the control of the Kip1 promoter.

2. The process according to claim 1, wherein the detector gene is a Kip1 gene.

3. The process according to claim 1, wherein the detector gene is the luciferase gene.

4. The process according to claim 1, wherein the target cells express the human Ah receptor.

5. The process according to claim 4, wherein the target cell is a transgenic cell, wherein the genome contains foreign detector gene DNA which is under the control of the Kip1 promoter.

6. The process according to claim 5, wherein the genome contains DNA which encodes expression of the human Ah receptor.

* * * * *